United States Patent [19]

Takatsu et al.

[11] Patent Number: 4,944,305
[45] Date of Patent: Jul. 31, 1990

[54] BLOOD PRESSURE MONITORING APPARATUS

[75] Inventors: Nariyasu Takatsu; Hidenobu Nakashima, both of Kasugai, Japan

[73] Assignee: Colin Electronics Co., Ltd., Aichi, Japan

[21] Appl. No.: 343,522

[22] Filed: Apr. 20, 1989

[51] Int. Cl.$^5$ .............................................. A61B 5/02
[52] U.S. Cl. ..................................... 128/683; 128/680
[58] Field of Search .......................... 128/672, 677–686

[56] References Cited

U.S. PATENT DOCUMENTS 4,144,879  3/1979  Nakayama et al. ................. 128/680
4,367,751  1/1983  Link et al. ............................ 128/682
4,774,960  10/1988  Arnold et al. ........................ 128/681

Primary Examiner—Angela D. Sykes
Attorney, Agent, or Firm—Oliff & Berridge

[57] ABSTRACT

A blood pressure monitoring apparatus for repetitively measuring blood pressure of a subject, including a measuring device for measuring a blood pressure of the subject at each of repetitive measuring cycles, and a display device for displaying a time-wise varying trend of the repetitively measured blood pressures in a two-dimensional table defined by a first axis indicative of time and a second axis indicative of blood pressure.

18 Claims, 4 Drawing Sheets

BLOOD PRESSURE MONITORING APPARATUS

BACKGROUND OF THE INVENTION

1. Field of the Invention

The present invention generally relates to a blood pressure monitoring apparatus for repetitively measuring blood pressure of a subject, and particularly such an apparatus which has a display device for displaying the repetitively measured blood pressures.

2. Discussion of the Prior Art

Blood pressure of a living body usually varies a comparatively large amount in a day, and also may be varied as a result of administration of medicine, for example. Therefore, it is carried out to measure and record a blood pressure of an inpatient three times or so per day. In the case of a patient whose blood pressure should be monitored, a nurse attending on the patient has to measure the blood pressure more frequently. This is a comparatively heavy burden on her. Thus, there has been known a blood pressure monitoring apparatus for repetitively measuring and displaying blood pressure of a subject.

However, the known monitoring apparatus is adapted to display, at regular intervals, the repetitively measured blood pressures together with the times at which the blood pressures have been measured. Accordingly the prior art apparatus does not permit the user to readily grasp a time-wise varying trend of the repetitively measured blood pressures, particularly in the case where the blood pressure measurements are effected at irregular time intervals or at regular intervals of a comparatively long time.

SUMMARY OF THE INVENTION

It is therefore an object of the present invention to provide a blood pressure monitoring apparatus which permits the user to readily grasp a time-wise varying trend of blood pressure.

The above object has been achieved by the present invention, which provides a blood pressure monitoring apparatus for repetitively measuring blood pressure of a subject, comprising measuring means for measuring a blood pressure of the subject at each of repetitive measuring cycles, and display means for displaying a time-wise varying trend of the repetitively measured blood pressures in a two-dimensional table defined by a first axis indicative of time and a second axis indicative of blood pressure.

In the blood pressure monitoring apparatus constructed as described above, the repetitively measured blood pressures of the subject are time-wise displayed in the two-dimensional table defined by the first axis indicative of time and the second axis indicative of blood pressure which table is provided by the display means. Thus, the user or operator can easily see the time-wise varying trend of the blood pressure of the subject, regardless of whether the blood pressure measurements are effected at regular or irregular time intervals and regardless of the length of the regular time intervals.

According to a feature of the present invention, the apparatus further comprises pressing means for pressing a body portion of the subject with a pressing force, the measuring means measuring, at each measuring cycle, variation in magnitude of heartbeat-synchronous pulses of the subject while the pressing force of the pressing means is varied, and determining a blood pressure of the subject based on the measured magnitude variation of the heartbeat-synchronous pulses. As the heartbeat-synchronous pulses, pulses of pulse wave preferably are utilized. The pulses of pulse wave are transmitted from the body portion to the measuring means synchronously with heartbeat of the subject. The magnitude variation of the heartbeat-synchronous pulses is measured either while the pressing force of the pressing means is decreased or increased.

According to another feature of the invention, the repetitive measuring cycles have a predetermined cycle time, the predetermined cycle time falling in a range of 5 to 30 minutes.

According to yet another feature of the invention, the display means displays, at each measuring cycle, the time-wise varying trend of the repetitively measured blood pressures such that the varying trend includes all the blood pressures that have been measured before, and at, the each measuring cycle.

According to a further feature of the invention, the display means includes means for determining, if the blood pressure measured at the each measuring cycle does not fall in a range defined between a preceding pair of upper and lower limits of the second axis of the two-dimensional table which have been used at at least a measuring cycle preceding the each measuring cycle, another pair of upper and lower limits of the second axis according to a first predetermined relationship between blood pressure and the upper limit and a second predetermined relationship between blood pressure and the lower limit based on the blood pressure measured at the each measuring cycle, such that all the blood pressures that have been measured before, and at, the each measuring cycle fall in a range defined between the another pair of upper and lower limits, replacing the preceding pair of upper and lower limits with the another pair of upper and lower limits, and displaying the another pair of upper and lower limits in the vicinity of opposite ends of the second axis of the two-dimensional table, respectively. It is preferred that the display means includes means for determining an initial pair of upper and lower limits of the second axis of the two-dimensional table according to the first and second predetermined relationships based on the blood pressure measured at a first measuring cycle after activation of the monitoring apparatus, such that the blood pressure falls in a range defined between the initial pair of upper and lower limits. It is also preferred that the display means includes means for preparing display data indicative of the time-wise varying trend of the repetitively measured blood pressures according to a currently effective pair of upper and lower limits of the second axis based on plural sets of blood pressure data each indicative of a corresponding one of the repetitively measured blood pressures and a time of measurement of the corresponding one blood pressure, and a display for displaying the time-wise varying trend according to the display data. It is recommended that the display comprises a display matrix consisting of a multiplicity of liquid-crystal display elements and having predetermined dimensions.

In a preferred embodiment of the invention, the apparatus further comprises a clock circuit for measuring time, and means for displaying the measured times at regular intervals along the first axis of the two-dimensional table while the measuring means measures the blood pressure of the subject at the repetitive measuring cycles, the first axis having a length corresponding to a predetermined monitoring period, the predetermined monitoring period falling in a range of 12 to 48 hours.

In another embodiment of the apparatus of the invention, the display means comprises means for displaying, by digits, the blood pressure measured at each measuring cycle.

In yet another embodiment of the apparatus of the invention, the measuring means measures, at each of the repetitive measuring cycles, a maximum, a minimum and an average blood pressure of the subject, the display means displaying the time-wise varying trend of each of the repetitively measured maximum, minimum and average blood pressures.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings, in which.

DETAILED DESCRIPTION OF THE PREFERRED EMBODIMENT

Figure 1:
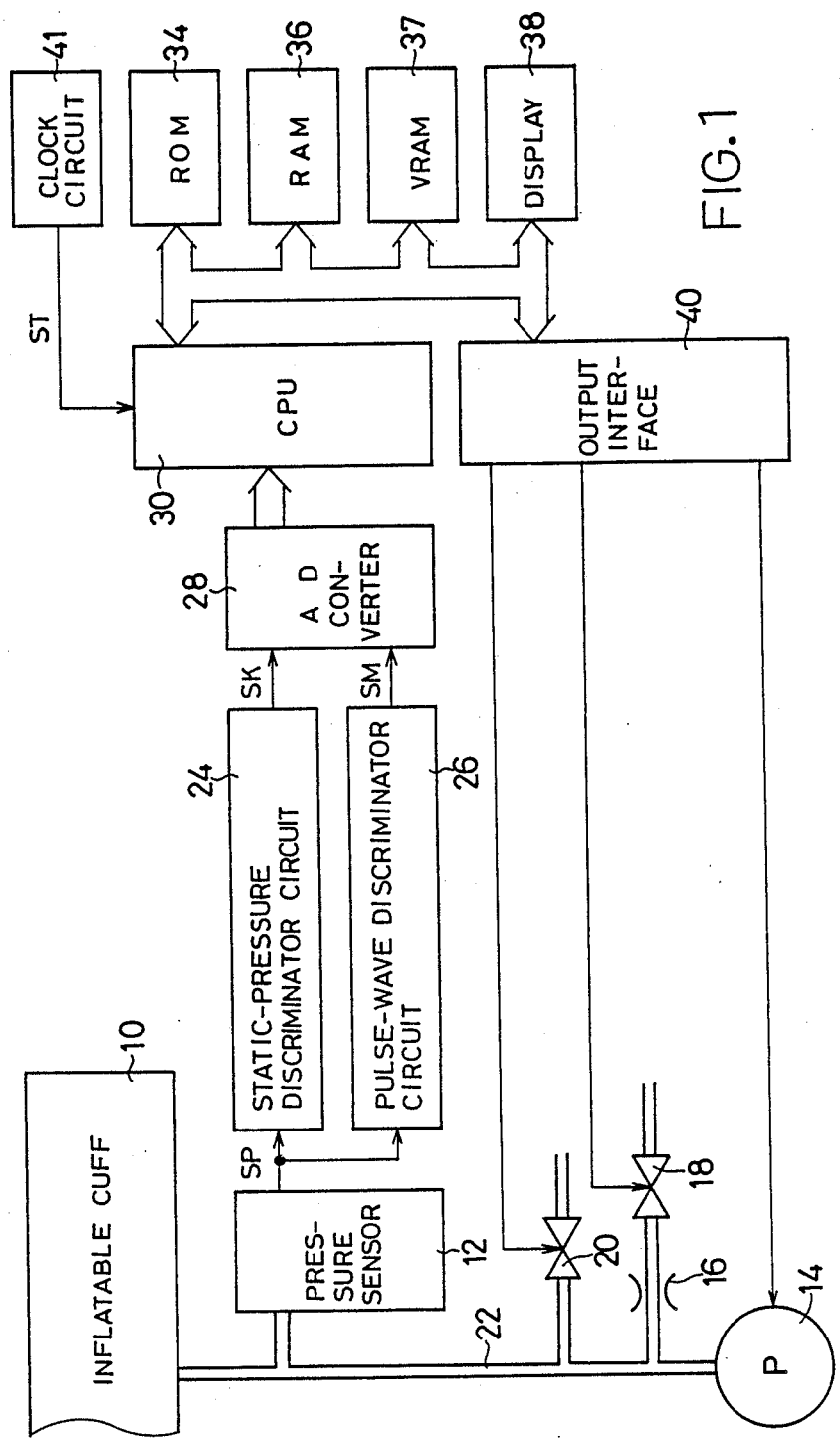
FIG. 1 is a diagrammatic view illustrating a blood pressure monitoring apparatus embodying the present invention.

Referring first to FIG. 1, there is illustrated a blood pressure monitoring apparatus embodying the present invention. In the figure reference numeral 10 designates an inflatable cuff formed of rubber and having an airtight, bag-like structure. The cuff 10 is set around an upper arm of a subject so as to press the upper arm. The cuff 10 is connected via a piping 22 to a pressure sensor 12, an air pump 14, a slow-deflation restrictor 16 and a slow-deflation electromagnetic valve 18, and a rapid-deflation electromagnetic valve 20.

The pressure sensor 12 detects pressure P in the cuff 10, and generates pressure signal SP representing the detected pressure P to a static-pressure discriminator circuit 24 and a pulse-wave discriminator circuit 26. The static-pressure discriminator circuit 24 includes a low-pass filter (not shown) for separating, from pressure signal SP, signal (cuff-pressure signal SK) representing static pressure in the cuff 10, and generates cuff-pressure signal SK to a central processing unit (CPU) 30 via an analog-to digital (A/D) converter 28. The pulse-wave discriminator circuit 26 includes a band-pass filter (not shown) for separating, from signal SP, signal (pulse-wave signal SM) representing pulse wave, and generates pulse-wave signal SM to the CPU 30 via the A/D converter 28. The pulse wave is pressure wave transmitted from the upper arm to the cuff 10 pressed thereagainst synchronously with heartbeat of the subject. The pulse wave consists of pulses synchronous with subject's heartbeat. In the present embodiment, the pulses of pulse wave serve as the heartbeat-synchronous pulses.

The CPU 30 is coupled via data bus to a read only memory (ROM) 34, a random access memory (RAM) 36 and a video random access memory (VRAM) 37, a display device 38, an output interface 40 and a clock circuit 41. The display device 38 has a START button 42 and a STOP button 44 (Fig. 6) for activating and deactivating the present apparatus to initiate and terminate a blood pressure monitoring of the subject, respectively. The clock circuit 41 measures a current time, and generates current-time signal ST to the CPU 30. The CPU 30 processes the received signals according to software programs pre-stored in the ROM 34 by utilizing temporary-storage function of the RAM 36. The CPU 30 controls the operation of each of the air pump 14 and the electromagnetic valves 18, 20. Also, the CPU 30 effects, at each of repetitive blood pressure measuring cycles, a series of steps for determining a maximum, a minimum and an average blood pressure of the subject based on pulse-wave signal SM, cuff-pressure signal SK and current-time signal ST. The RAM 36 stores plural sets of blood pressure data each indicative of the maximum, minimum and average blood pressures determined at a corresponding one of the repetitive measuring cycles, and a time of measurement of the three blood pressures. The VRAM 37 stores video data indicative of a time-wise varying trend of each of the maximum, minimum and average blood pressures measured at the repetitive measuring cycles. The display device 38 includes a display matrix 46 (FIG. 6) consisting of a multiplicity of liquid-crystal display elements and having predetermined dimensions of length and width. The display matrix 46 includes a first display portion 47 for indicating by digits a maximum blood pressure 47a, an average blood pressure 47b and a minimum blood pressure 47c determined at each measuring cycle. The display matrix 46 also includes a second display portion 48 for indicating, according to the video data stored in the VRAM 37, the blood pressure time-wise varying trends in a two-dimensional table 49 defined by an x axis 49a indicative of time and and a y axis 49b indicative of blood pressure. The video data consists of plural sets of image data corresponding to a plurality of image elements provided by the liquid-crystal display elements of the matrix 46.

Figure 2:
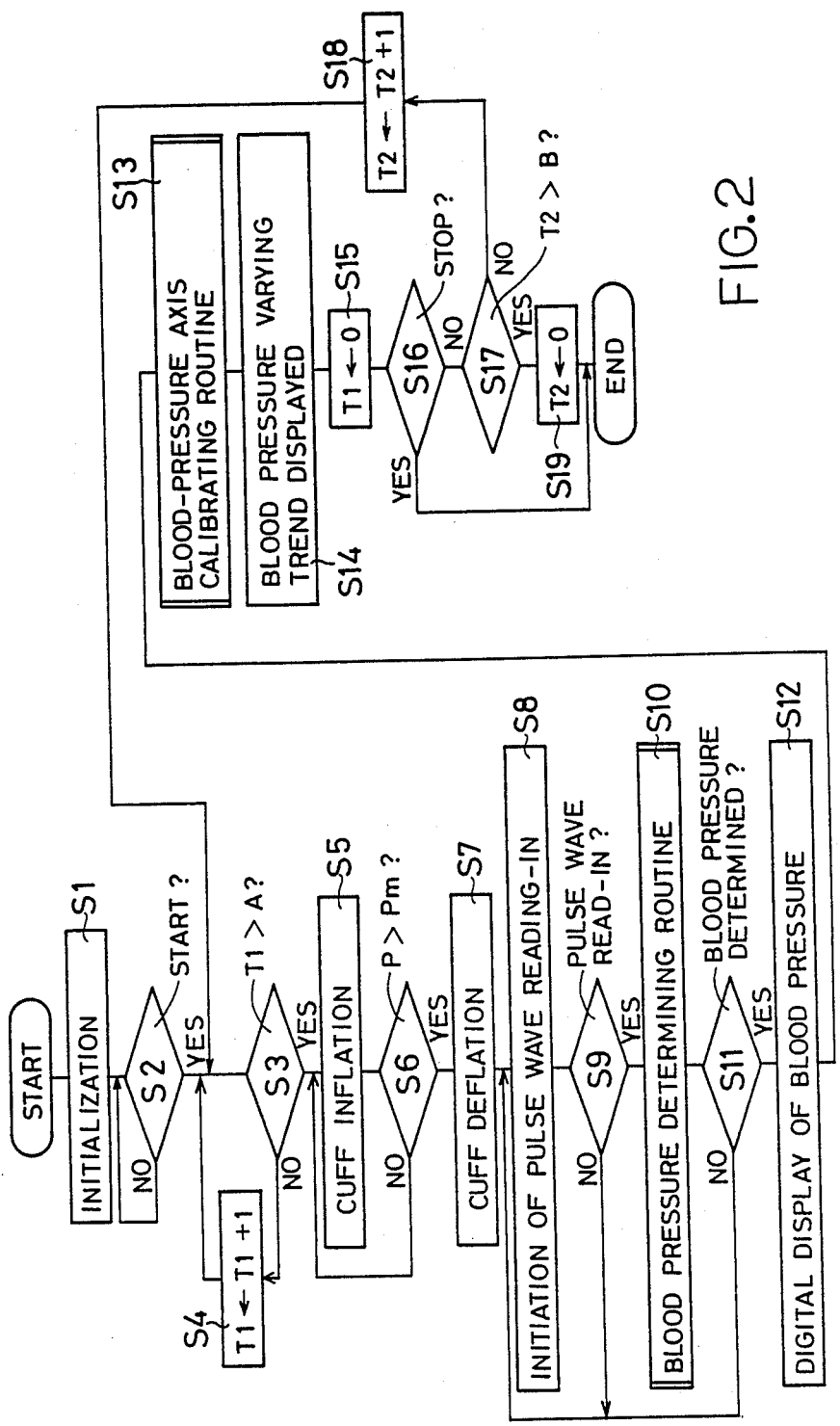
FIG. 2 is a flow chart illustrating the operation of the apparatus of FIG. 1.

Referring next to FIG. 2 there is illustrated the flow chart according to which the present blood pressure monitoring apparatus is operated.

Upon application of electric power to the apparatus, the control of the CPU 30 goes to step S1 at which the initialization of the apparatus is effected. Step S1 is followed by step S2 at which it is judged whether or not the START button 42 has been depressed. If the judgement at step S2 is negative, step S2 is repeated until the judgement is turned affirmative, namely, until the START button 42 is operated. Meanwhile, if the judgement at step S2 is affirmative, the control of the CPU 30 goes to step S3 at which it is judged whether or not count or content of a first timer T1 has exceeded a reference value A. Reference value A represents a predetermined cycle time of the repetitive measuring cycles. In other words, the present apparatus measures a blood pressure of the subject at regular time intervals.

The cycle time is predetermined to fall in the range of 5 to 30 minutes.

If the judgement at step S3 is negative, the control of the CPU 30 goes to step S4 at which the content of first timer T1 is incremented by one. Steps S3 and S4 are repeated until the content of first timer T1 reaches reference value A. Meanwhile, if the judgement at step S3 is affirmative, the control of the CPU 30 goes to step S5 at which both the electromagnetic valves 18 and 20 are closed and the air pump 14 is activated, so that pressure P in the cuff 10 (hereinafter, referred to as "cuff pressure P") is increased.

Step S5 is followed by step S6 at which cuff pressure P has reached a target pressure level Pm which is predetermined to be sufficiently higher than an estimated maximum blood pressure of the subject, for example 180 mmHg. If the judgement at step S6 is negative, steps S5 and S6 are repeated until cuff pressure P reaches target level Pm. Meanwhile, if the judgement at step S6 is affirmative, the control of the CPU 30 goes to step S7 at which the air pump 14 is deactivated and the slow-deflation valve 18 is opened, so that cuff pressure P is decreased at a comparatively low rate.

Step S7 is followed by step S8 at which the CPU 30 begins reading in pulse wave represented by signal SM supplied through the pulse wave discriminator circuit 26. Step S8 is followed by step S9 at which it is judged whether or not a pulse of pulse wave has been detected and supplied in the form of pulse wave signal SM to the CPU 30. If the judgement at step S9 is negative, steps S8 and S9 are repeated. Meanwhile, if the judgement at step S9 is affirmative, the control of the CPU 30 goes to step S10, a blood pressure determining routine.

The blood pressure determining routine of step S10 is constituted by the algorithom for determining a maximum and a minimum blood pressure by the well-known oscillometric method. In the oscillometric method, a maximum and/or a minimum blood pressure are/is determined based on a cuff pressure (P) at the time of detection of a pulse (of pulse wave) whose magnitude or amplitude is significantly largely changed as compared with that of the preceding or following pulse. Thus, at step S10 a maximum and a minimum blood pressure of the subject are determined based on pulse wave signal SM and cuff pressure signal SK. An average blood pressure is determined based on the thus determined maximum and minimum blood pressures. An average of the times at which the two pulses corresponding to the maximum and minimum blood pressures are detected, is used as the time of measurement of the maximum, minimum and average blood pressures, and stored as blood pressure data in the RAM 36 together with the three blood pressures.

Figure 6:
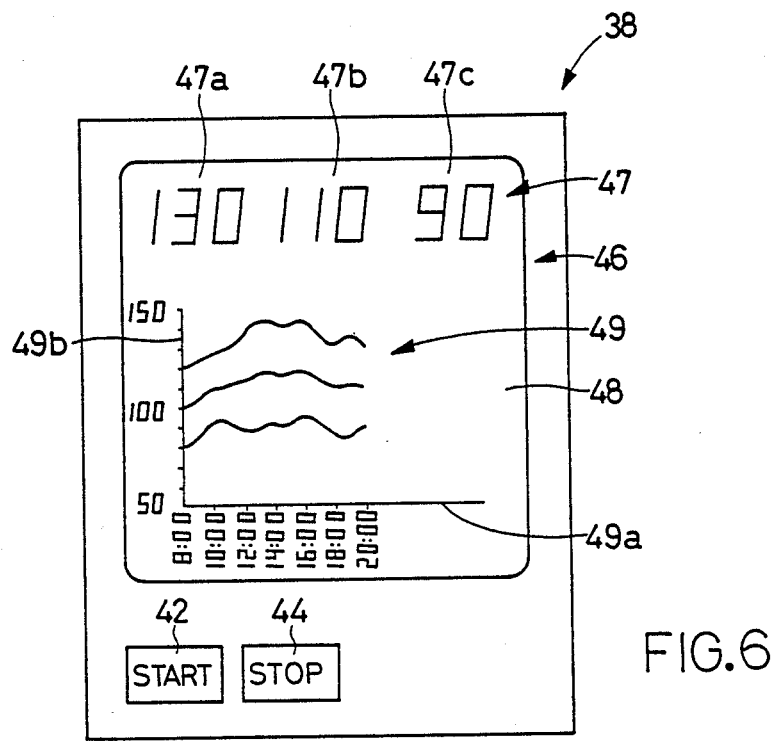
FIG. 6 is a plan view illustrating the display device of the apparatus of FIG. 1 which displays a time-wise varying trend of the blood pressure of the subject in the two-dimensional table provided thereby.

Step S10 is followed by step S11 at which it is judged whether or not the blood pressures of the subject have been determined. If the judgement at step S11 is negative, steps S8 through S11 are repeated. Meanwhile, if the judgement at step S11 is affirmative, the control of the CPU 30 goes to step S12 at which the maximum, average and minimum blood pressures are displayed by digits in the first display portion 47 (47a, 47b, 47c) of the display matrix 46 of the display device 38, as shown in FIG. 6.

Figure 3:
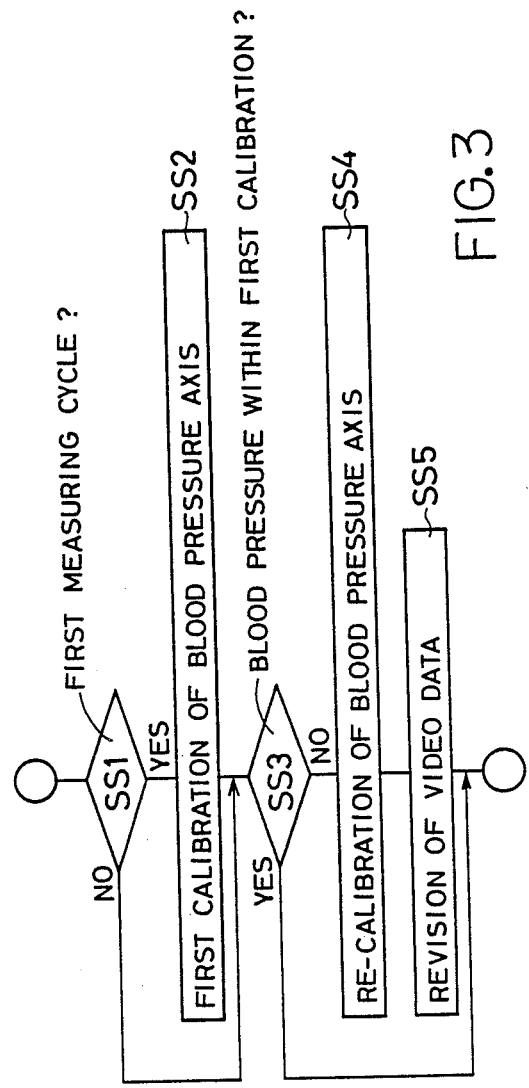
FIG. 3 is a flow chart illustrating the blood pressure-axis calibrating routine of the flow chart of Fig. 2.

Step S12 is followed by step S13, a blood pressure-axis calibrating routine illustrated in detail in FIG. 3. First, at step SS1 it is judged whether or not the current measuring cycle is a first measuring cycle after the present apparatus is activated by operation of the START button 42. If the judgement at step SS1 is negative, the control of the CPU 30 skips step SS2 and goes to step SS3. Meanwhile, if the judgement at step SS1 is affirmative, the control of the CPU 30 goes to step SS2 at which an initial pair of upper and lower limits UL and LL of the y axis 49b(hereinafter, referred to as "blood pressure-axis 49b") of the two-dimensional table 49 are determined according to a predetermined first relationship between maximum blood pressure and upper limit UL and a predetermined second relationship between minimum blood pressure and lower limit LL, both shown in FIGS. 4 and 5, based on the maximum and minimum blood pressures determined at the current (i.e., first) measuring cycle, respectively. Therefore, a blood pressure which does not fall in the range defined between the initial pair of upper and lower limits, cannot be displayed in the two-dimensional table 49, unless the initial pair of upper and lower limits are replaced with another pair of upper and lower limits which permit the blood pressure in question to fall in the range defined therebetween, namely, unless the blood-pressure axis 49b is re-calibrated. The initial pair of upper and lower limits are stored in the RAM 36. Step SS2 is followed by step SS3.

At step SS3 it is judged whether or not both the maximum and minimum blood pressures determined at step S10 fall in the range defined between the pair of upper and lower limits UL, LL which are currently stored in the RAM 36. If the current measuring cycle is the first measuring cycle, it goes without saying that the judgement at step SS3 is affirmative, and the control of the CPU 30 skips steps SS4 and SS5 to go to step S14 of the flow chart of FIG. 2. Meanwhile, if at least one of the maximum and minimum blood pressures determined at the current measuring cycle other than the first measuring cycle, does not fall in the range defined between a preceding pair of upper and lower limits of the blood-pressure axis 49b used at at least the preceding measuring cycle, namely, if the judgement at step SS3 is affirmative, step SS3 is followed by step SS4 at which a new pair of upper and lower limits of the blood-pressure axis 49b are determined according to the first and second relationships of FIGS. 4 and 5 based on the maximum and minimum blood pressures determined at the current measuring cycle, respectively, such that all the maximum and minimum (and average) blood pressures fall in the range defined between the new pair of upper and lower limits. The new pair of upper and lower limits are stored in the RAM 36 in place of the preceding pair of upper and lower limits. Thus, the blood-pressure axis 49b of the two-dimensional table 49 is re-calibrated. Step SS4 is followed by step SS5 at which the video data stored in the VRAM 37 is revised according to the re-calibrated blood-pressure axis 49b and the plural sets of blood pressure data stored in the RAM 36.

The blood pressure-axis calibrating routine of step S13 is terminated at step SS5, and step SS5 is followed by step S14 of FIG. 2. At step S14 a set of blood pressure data indicative of the maximum, minimum and average blood pressures determined at step S10 of the current measuring cycle and a time of measurement of the three blood pressures, is stored in the RAM 36 and added to the video data stored in the VRAM 37, and displayed or visualized in the two-dimensional table 49 according to the video data, namely, in the image elements (or by the liquid-crystal display elements) corresponding to the set of blood pressure data newly added to the video data. In the present embodiment, the display device 38, steps S13 and S14 stored in the form of software programs in the ROM 34, and the CPU 30, RAM 36 and VRAM 37 for effecting those steps, cooperate with each other to serve as the display means for displaying the time-wise varying trend of the blood pressure of the subject in the two-dimensional table defined by the first axis indicative of time and the second axis indicative of blood pressure.

Digits indicative of upper and lower limits UL, LL and intermediate values are displayed along the blood-pressure axis 49b, while digits indicative of times are displayed at regular intervals (for example, every two hours as shown in FIG. 6) along the time axis 49a.

Step S14 is followed by step S15 at which the content of first timer T1 is reset to zero, and at the following step S16 it is judged whether or not the STOP button 44 has been operated. If the judgement at step S16 is affirmative, the blood pressure monitoring is terminated. Meanwhile, if the judgement at step S16 is negative, the control of the CPU 30 goes to step S17 at which it is judged whether or not count or content of a second timer T2 has reached a second reference value B which represents a predetermined monitoring period in which the blood pressure of the subject is required to be monitored by the present apparatus. The monitoring period is predetermined to be 24 hours, for example. If the judgement at step S17 is negative, the control of the CPU 30 goes to step S18 at which the content of second timer T2 is incremented by one, and subsequently step S3 and the following steps are repeated at the following measuring cycle to measure a maximum, a minimum and an average blood pressure of the subject and display the measured blood pressures, in place of the blood pressures measured and displayed at the preceding measuring cycle, in the first display portion 47 of the display matrix 46. The measured blood pressures are also displayed in the second display portion 48 as a last portions of the maximum, minimum add average blood pressure time-wise varying trends.

If the judgement at step S17 is affirmative, the control of the CPU 30 goes to step S19 at which the content of second timer T2 is reset to zero, and the blood pressure monitoring is terminated.

As is apparent from the foregoing, in the present embodiment, the maximum, minimum and average blood pressures determined at the repetitive measuring cycles are time-wise displayed in the two-dimensional table 49 defined by the time axis 49a and the blood pressure axis 49b. Digits indicative of times are displayed every two hours along the time axis 40a, while digits indicative of upper and lower limits UL, LL and intermediate blood pressures are displayed along the blood-pressure axis 49b. Thus, the present blood pressure monitoring apparatus permits the user or the medical staff to more easily grasp the time-wise varying trend of the blood pressure of the subject than the conventional apparatus does.

Also, in the present embodiment, the blood pressure varying trend is displayed at each measuring cycle such that the varying trend includes a last blood pressure that has been measured at that measuring cycle. Even in the case of a comparatively long time monitoring, the user can readily see the blood pressure varying trend including a last blood pressure obtained at each measuring cycle, before the long time monitoring is terminated.

Figure 4:
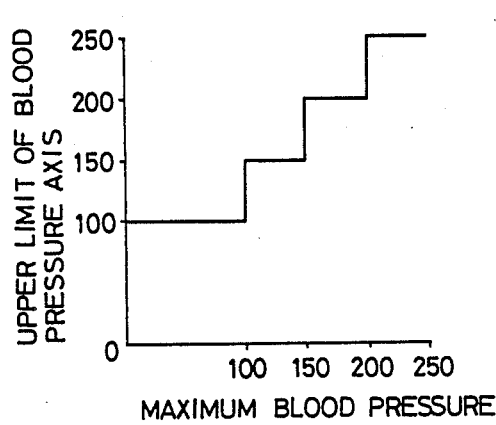
FIGS. 4 and 5 are graphs showing a relationship between maximum blood pressure and the upper limit of the blood-pressure axis of the two-dimensional table of a display device of the apparatus of FIG. 1, and a relationship between minimum blood pressure and the lower limit of the blood-pressure axis, respectively, the graphs being utilized when the apparatus is operated according to the flow chart of FIG. 3.
Figure 5:
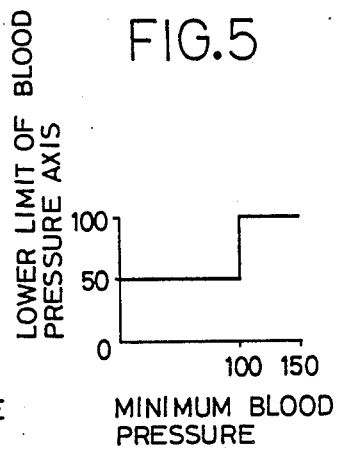

In the present embodiment, if at least one of the maximum and minimum blood pressures determined at a current measuring cycle does not fall in the range defined between the blood pressure upper and lower limits (for the y axis 49b of the two-dimensional table 49) used at at least the preceding measuring cycle, a new pair of upper and lower limits are determined according to the predetermined first and second relationships shown in FIGS. 4 and 5, such that all the blood pressures that have been measured at all the preceding measuring cycles and the current measuring cycle fall in the range defined between the new pair of upper and lower limits. In addition, the preceding video data according to which the blood pressure varying trend including the blood pressure obtained at the preceding measuring cycle is displayed on the display device 38, is revised according to the new pair of upper and lower limits of the blood pressure axis 49b. Thus, the present apparatus automatically calibrates the blood pressure axis 49b so as to adapt to not only a comparatively large variation in blood pressure of a subject during a monitoring period but also different subjects having different blood pressuretively. Consequently, the user obtains a clear time-wise varying trend of subject's blood pressure.

Further, in the present embodiment, a maximum, a minimum and an average blood pressure are displayed by digits at each measuring cycle in the first display portion 47 of the display matrix 46. Thus, the blood pressures at present are readily grasped by the user without following or watching the second display portion 48 displaying the blood pressure varying trend in the two-dimensional table 49.

While in the illustrated embodiment the display matrix of the display device 38 is constituted by the liquid-crystal display elements, it is possible to use other display devices including light emitting diodes or a cathode ray tube (CRT), for example.

Although in the illustrated embodiment the time-wise varying trend of the blood pressure is displayed on a real-time basis, namely, such that the varying trend includes last blood pressures that have been measured at the current (or preceding) measuring cycle, it is possible to display the blood pressure varying trend after the blood pressure monitoring is terminated with an elapse of the predetermined monitoring period (represented by second reference value B).

In the illustrated embodiment, it is possible to omit steps SS1 and SS2 of the flow chart of FIG. 3 in the case where a predetermined initial pair of upper and lower limits are displayed along the blood pressure axis 49b upon the operation of the START button 42. In this case, the initial pair of upper and lower limits are predetermined based on normal maximum and minimum blood pressures.

While in the illustrated embodiment second reference value B is predetermined to correspond to a time period of 24 hours, it is possible to predetermine second reference value B to correspond to 12 hours or 48 hours.

While in the illustrated embodiment the repetitive measuring cycles have a predetermined cycle time, it is possible to manually effect repetitive blood pressure measurements by operating an activation button at irregular time intervals.

Although in the illustrated embodiment the maximum, minimum and average blood pressure are time-wise displayed in the second display portion 49 of the display matrix 46, it is possible to adapt the apparatus to display only one or two of the three blood pressures.

In the illustrated embodiment, times and blood pressures are displayed by digits along the time and blood pressure axes 49a, 49b of the two-dimensional table 49, respectively. However, it is possible to fix digits indicative of predetermined times and blood pressures by pre-printing the digits on an outer surface of a housing of the display device 38.

While in the illustrated embodiment a maximum, a minimum and an average blood pressure determined at each measuring cycle are displayed by digits in the first display portion 47 of the display matrix 46, it is possible to omit the first display portion 47.

Furthermore, while in the illustrated embodiment the time-wise varying trends of the blood pressures are displayed by graphs of broken lines, it is possible to display the varying trends by a plurality of bars each of which indicates a maximum blood pressure at an upper end thereof, a minimum blood pressure at a lower end thereof and an average blood pressure at a middle point thereof.

Although in the illustrated embodiment the blood pressure determining routine of step S10 of FIG. 2 is efffected on a real-time basis, namely, each time a pulse of pulse wave is detected, it is possible to effect the routine on a "batch" basis, namely, after all the pulses of pulse wave have been detected while cuff pressure P is decreased at the comparatively low rate.

While in the illustrated embodiment the blood pressure determining routine of step S10 of FIG. 2 is effected while cuff pressure P is decreased, it is possible to effect the determining routine while cuff pressure P is increased.

Although in the illustrated embodiment pulses of pulse wave are utilized as the heartbeat-synchronous pulses, it is possible to utilize, as the heartbeat-synchronous pulses, Korotkoff sounds produced from an arterial vessel pressed under an inflatable cuff.

While in the illustrated embodiment is used the inflatable cuff which is wound around an upper arm of a subject, it is possible to use a pulse wave sensor of a type which is pressed against an arterial vessel via body surface of a subject, so as to detect variation in magnitude (or amplitude) of pulses of pulse wave and thereby determine a maximum, a minimum and an average blood pressure of the subject.

Although in the illustrated embodiment the current time measured by the clock circuit 41 is displayed at regular intervals along the time axis 49a of the two-dimensional table 49, it is possible to employ a timer device of a type which begins measuring an elapsed time after a START button is operated to activate the monitoring apparatus. In this case, the elapsed times measured after the time at which the START button is operated, are displayed along the time axis 49a.

While the present invention has been described in its presently preferred embodiment with detailed particularities, it is to be understood that the invention may be embodied with various modifications, changes and improvements that may occur to those skilled in the art without departing from the scope and spirit of the invention defined in the appended claims.

What is claimed is:

1. A blood pressure monitoring apparatus for repetitively measuring blood pressure of a subject, comprising:
   measuring means for measuring at least one of a maximum, a minimum and an average blood pressure of a subject at each of repetitive measuring cycles; and
   display means for displaying a time-wise varying trend of said at least one of maximum, minimum and average blood pressure, by indicating a graph representing the repetitively measured values of said at least one blood pressure in a two-dimensional table defined by a first axis indicative of time and a second axis indicative of blood pressure.

2. The apparatus as set forth in claim 1, further comprising
   pressing means for pressing a body portion of the subject with a pressing force,
   said measuring means measuring, at each measuring cycle, variation in magnitude heartbeat-synchronous pulses of the subject while the pressing force of said pressing means is varied, and determining a value of said at least one blood pressure of the subject based on the measured magnitude variation of said heatbeat-synchronous pulses.

3. The apparatus as set forth in claim 2, wherein said heartbeat-synchronous pulses consist of pulses of pulse wave, the pulse of said pulse wave being transmitted from said body portion to said measuring means synchronously with heartbeat of the subject.

4. The apparatus as set forth in claim 2, wherein said measuring means measures, at each measuring cycle, the magnitude variation of said heartbeat-synchronous pulses while the pressing force of said pressing means is decreased.

5. The apparatus as set forth in claim 2, wherein said measuring means measures, at each measuring cycle, the magnitude variation of said heartbeat-synchronous pulses while the pressing force of said pressing means is increased.

6. The apparatus as set forth in claim 1, wherein said repetitive measuring cycles have a predetermined cycle time, said predetermined cycle time falling in a range of 5 to 30 minutes.

7. The apparatus as set forth in claim 1, wherein said display means displays, at each measuring cycle, the time-wise varying trend of said at least one blood pressure by indicating in said two dimensional table the graph representing all the values of said at least one blood pressure that have been measured before, and at, said each measuring cycle.

8. The apparatus as set forth in claim 7, wherein said display means includes
   means for preparing display data indicative of the time-wise varying tread of said at least one blood pressure according to an upper and a lower limit of said second axis of said two dimension table based on plural sets of blood pressure data each indicative of a corresponding one of said repetitively measured values of said at least one blood pressure and a time of measurement of the corresponding one blood pressure value, and
   a display for displaying the time-wise varying trend of said at least one blood pressure by indicating said graph according to said display data.

9. The apparatus as set forth in claim 8, wherein said display comprises a display matrix consisting of a multiplicity of liquid-crystal display elements, said display matrix having predetermined dimensions.

10. The apparatus as set forth in claim 7, further comprising:
    a clock circuit for measuring times,
    said display means displaying the measured times at regular intervals of length along said first axis of said two-dimensional table while said measuring means measures the values of said at least one blood pressure of the subject at said repetitive measuring cycles,
said first axis having a length corresponding to a predetermined monitoring period, said predetermined monitoring period falling in a range of 12 to 48 hours.

11. The apparatus as set forth in claim 1, wherein said display means comprises
means for displaying, by digits, the value of said at least one blood pressure measured by said measuring means at each measuring cycle.

12. The apparatus as set forth in claim 1, wherein said measuring means measures, at each measuring cycle, said maximum, minimum and average blood pressures of the subject,
said display means displaying the time-wise varying trends of the maximum, minimum and average blood pressures of the subject by indicating corresponding graphs in said two dimensional table.

13. A blood pressure monitoring apparatus, comprising:
measuring means for measuring at least one of a maximum, a minimum and an average blood pressure of a subject at each of repetitive measuring cycles;
display means for displaying a time-wave varying trend of said at least one of maximum, minimum and average blood pressures, by indicating a graph representing the repetitively measured values of said at least one blood pressure in a two-dimensional table defined by a first axis indicative of time and a second axis indicative of blood pressure;
calibrating means for calibrating said second axis of said two-dimensional table by adjusting an upper and a lower limit of said second axis, said calibrating means determining, if a value of said at least one blood pressure measured at each measuring cycle does not fall in a range defined between a preceding pair of upper and lower limits of said second axis which have been used at at least a measuring cycle preceding said each measuring cycle, another pair of upper and lower limits according to a first predetermined relationship between blood pressure and second-axis upper limit and a second predetermined relationship between blood pressure and second-axis lower limit, respectively, based on the value of said at least one blood pressure measured at said each measuring cycle, such that all the values of said at least one blood pressure that have been measured before, and at, said each measuring cycle fall in a range defined between said another pair of upper and lower limits; and
said display means displaying, in place of said preceding pairs of upper and lower limits, said another pair of upper and lower limits in the vicinity of corresponding ends of said second axis, and displaying said time-wise varying trend in the two-dimensional table having the second axis calibrated with said another pair of upper and lower limits.

14. The apparatus as set forth in claim 13, wherein said measuring means measures a maximum and a minimum blood pressure of the subject at each measuring cycle, said calibrating means determining said another pair of upper and lower limits according to a first predetermined relationship between maximum blood pressure and second-axis upper limit and a second predetermined relationship between minimum blood pressure and second-axis lower limit based on the corresponding maximum and minimum blood pressures measured by said measuring means, respectively, said display means displaying the time-wise varying trends of each of said maximum and minimum blood pressures of the subject, and the time-wise varying trend of an average blood pressure of the subject which trend is determined based on the maximum and minimum blood pressure time-wise varying trends.

15. The apparatus as set forth in claim 13, wherein said display means includes means for determining an initial pair of upper and lower limits of said second axis of said two-dimensional table according to said first and second predetermined relationships based on a value of said at least one blood pressure measured at a first measuring cycle after activation of the monitoring apparatus, such that the measured value of said at least one blood pressure falls in a range defined between said initial pair of upper and lower limits.

16. The apparatus as set forth in claim 13, wherein said display means includes means for preparing display data indicative of the time-wise varying trend of said at least one blood pressure according to a currently effective pair of upper and lower limits of said second axis of said two-dimensional table based on plural sets of blood pressure data each indicative of a corresponding one of the repetitively measured values of said at least one blood pressure and a time of measurement of the corresponding one blood pressure value, and
a display for displaying the time-wise varying trend of said at least one blood pressure by indicating said graph according to said display data.

17. The apparatus as set forth in claim 16, wherein said display comprises a display matrix consisting of a multiplicity of liquid-crystal display elements, said display matrix having a predetermined length and a predetermined width.

18. The apparatus as set forth in claim 13, further comprising
a clock circuit for measuring times,
said display means displaying the measured times at regular intervals of length along said first axis of said two-dimensional table as said measuring means measures values of said at least one blood pressure of the subject at said repetitive measuring cycles,
said first axis having a length corresponding to a predetermined monitoring period, said predetermined monitoring period falling in a range of 12 to 48 hours.

* * * * *